US007119248B1

(12) United States Patent
Rajewsky et al.

(10) Patent No.: US 7,119,248 B1
(45) Date of Patent: Oct. 10, 2006

(54) ANTIBODIES AGAINST EPITOPES WITH HOMOLOGY TO SELF ANTIGENS, METHODS OF PREPARATION AND APPLICATIONS THEREOF

(75) Inventors: Klaus Rajewsky, Cologne (DE); Werner Mueller, Cologne (DE); Juergen Roes, Cologne (DE)

(73) Assignee: Miltenyi Biotec GmbH, Bergisch Gladach (DE)

( * ) Notice: Subject to any disclaimer, the term of this patent is extended or adjusted under 35 U.S.C. 154(b) by 0 days.

(21) Appl. No.: 08/226,168

(22) Filed: Apr. 12, 1994

(51) Int. Cl.
*C12P 21/08* (2006.01)
*A01K 67/027* (2006.01)
*A61K 39/00* (2006.01)
*C12N 5/06* (2006.01)
*C07K 16/18* (2006.01)

(52) U.S. Cl. .................. 800/6; 800/4; 800/13; 800/18; 800/21; 424/184.1; 530/387.1; 530/388.1; 435/326

(58) Field of Classification Search ............. 530/388.1, 530/387.1; 424/184.1; 800/2, 18, 6, 21, 800/4, 13, 25; 935/89, 93; 435/326
See application file for complete search history.

(56) References Cited

FOREIGN PATENT DOCUMENTS

| WO | WO 90/03432 | 4/1990 |
| WO | WO 94/09117 | 4/1994 |
| WO | WO 94/24274 | 10/1994 |

OTHER PUBLICATIONS

Miltenyi et al Cytometry 11: 231, 1990.*
Roes et al. Int. Immunol 3: 1367, 1991, Sites in *Basic & Clinical Annulogy*, 1983, pp. 32 & 336-343.*
Prusin et al PNAS 90: 10608, 1993.*
Biotechnology, vol. 10: 534-539, 1992.*
Seamark et al., "Progress and Emerging Problems in Livestock Transgenesis: a Summary Perspective," Reprod. Fertil. Dev., vol. 6: 653-657, 1994.*
Mullins et al., "Perspective Series: Molecular Medicine in Genetically Engineered Animals," J. of Clin. Invest., vol. 98(11), Suppl.: S37-S40, 1996.*
Kappel et al., "Regulating Gene Expression in Transgenic Animals," Current Opinion in Biotechnology,vol. 3: 548-553, 1992.*
Rudich et al. (1988) J. Exp. Med., vol. 168 (1), 247-266, 1988.*
Merriam Webster; Medical Dictionary, 1997: Definition of autologous.*
Kessler et al. (1979) J. Immunol., vol. 123, No. 6, 2772-2778.*
Marshak-Rothstein et al. (1979) J. Immunol., vol. 122, No. 6, 2491-2497.*
Kessler et al., "Membrane orientation and location of multiple and distinct allotypic determinants of mouse lymphocyte IgD" *J. Immunol.* (1979) 123:2772-2778.
Reif et al., "The AKR thymic antigen and its distribution in leukemias and nervous tissues" *J. Exp. Med.* (1964) 129:413-433.

Marshak-Rothstein, "Properties and applications of monoclonal antibodies directed against determinants of the thy-I locus" *J. Immunol.* (1979) 122:2491-2497.
Oi et al., "Localization of murine Ig-Ib and Ig-Ia ($IgG_{2a}$) allotypic determinants detected with monoclonal antibodies" *Mol. Immunol.* (1979) 16:1005-1017.
Mansour et al., "Disruption of the proto-oncogene int-2 in mouse embryo-derived stem cells: a general strategy for targeting mutations to non-selectable genes" *Nature* (1988) 336:348-352.
Kitamura et al., "A B cell-deficient mouse by targeted disruption of the membrane exon of the immunoglobin μ chain gene" *Nature* (1991) 350:423-426.
Shinkai et al., "Restoration of T cell development in RAG-2-deficient mice by functional TCR transgenes" *Science* (1993) 259:822-825.
Komori et al., "Lack of N regions in antigen receptor variable region genes of TdT-deficient lymphocytes" *Science* (1993) 261:1171-1175.
Dialog™ Computer Abstract of International (PCT) Patent Publication No. WO 91/10741 (Jul. 25, 1991).
Dialog™ Computer Abstract of German Patent No. DE P4228162.8 (Aug. 25, 1992).
Miltenyi et al., "High gradient magnetic cell separation with MACS" *Cytometry* (1990) 11:231-238.
Roes et al., "Immunoglobulin D (IgD)-deficient mice reveal an auxiliary receptor function for IgD in antigen-mediated recruitment of B cells" *J. Exp. Med.* (1993) 177:45-55.
Roes et al., "Cell autonomous expression of IgD is not essential for the maturation of conventional B cells" *Int. Immunol.* (1991) 3:1367-1371.
Hemperly et al., "Sequence of a cDNA clone encoding the polysialic acid-rich and cytoplasmic domains of the neural cell adhesion molecule N-CAM" *Proc. Natl. Acad. Sci. USA* (1986) 83:3037-3041.
Barthels et al., "Isolation and nucleotide sequence of mouse NCAM cDNA that codes for a M, 79 000 polypeptide without a membrane-spanning region" *EMBO J.* (1987) 6:907-914.
Barthels et al., "High degree of NCAM diversity generated by alternative RNA splicing in brain and muscle" *Eur. J. Neurosci.* (1992) 4:327-337.
Crossin et al., "Expression of adhesion molecules and the establishment of boundaries during embryonic and neural development" *Exp. Neurol.* (1990) 109:6-18.
Tosney et al., "The distribution of NCAM in the chick hindlimb during axon outgrowth and synaptogenesis" *Dev. Biol.* (1986) 114:437-452.

(Continued)

*Primary Examiner*—Anne M Wehbé
(74) *Attorney, Agent, or Firm*—Townsend and Townsend and Crew LLP

(57) ABSTRACT

This invention provides novel methods of obtaining autologous monoclonal antibodies (AMABs) to self-antigens or homologs thereof. The method involves obtaining a genetically engineered host animal that does not biosynthesize at least one epitope of the antigen and utilizes the lack of self-tolerance of the host to the epitope to produce antibodies specific to the antigen. The invention also encompasses the AMABs produced by the methods. The invention further encompasses methods of isolating cells comprising the use of such AMABs that have specificity for a cell surface antigen.

8 Claims, 4 Drawing Sheets

OTHER PUBLICATIONS

Thiery et al., "Adhesion among neural cells of the chick embryo" *J. Biol. Chem.* (1977) 252:6841-6845.

Key et al., "Olfactory neurons express a unique glycosylated form of the neural cell adhesion molecule (N-CAM)" *J. Cell. Biol.* (1990) 110:1729-1743.

Chung et al., "Developmental expression of neural cell adhesion molecules in the mouse neocortex and olfactory bulb" *J. Comp. Neurol.* (1991) 314:290-305.

Theodosis et al., "Retention of embryonic features by an adult neuronal system capable of plasticity: polysialylated neural cell adhesion molecule in the hypothalamoneurohypophysial system" *Proc. Natl. Acad. Sci. USA* (1991) 88:5494-5498.

Morris, "Spatial localization does not require the presence of local cues" *Learn. Motiv.* (1981) 12:239-260.

Sieckmann, "The use of anti-immunoglobulins to induce a signal for cell division in B lymphocytes via their membrane IgM and IgD" *Immunol. Rev.* (1980) 52:181-210.

Stall et al., "Allotypic specificities of murine IgD and IgM recognized by monoclonal antibodies" *J. Immunol.* (1984) 132:787-795.

Reif et al., "Specificity of isoantisera against leukaemic and thymic lymphocytes" *Nature* (1963) 200:1332-1333.

Veis et al., "BcI-2-deficient mice demonstrate fulminant lymphoid apoptosis, polycystic kidneys, and hypopigmented hair" *Cell* (1993) 75:229-240.

Zitron et al., "Regulation of murine B cells through surface immunoglobulin" *J. Exp. Med.* (1980) 152:1135-1146.

Williamson et al., "Circumventing tolerance to generate autologous monoclonal antibodies to the prion protein" *Proc. Natl. Acad. Sci. USA* (1996) 93:7279-7282.

Declerck et al. "Generation of monoclonal antibodies against autologous proteins in gene-inactivated mice" J Biol Chem 270:8392-8400 (1995).

Doetschman et al. "Establishment of hamster blastocyst-derived embryonic stem (ES) cells" Dev. Biol. 127:221-227 (1988).

Evans. "Potential for the genetic manipulation of Mammals" Mol. Biol. Med. 6:557-565 (1989).

Evans et al. "Establishment in culture of pluripotential cells from mouse embryos" Nature 292:154-156 (1981).

First et al. "Systems for production of calves from cultured from bovine embryonic stem cells" Reprod. Fertil. Dev. 6:553-62 (1994).

Graves et al. "Derivation and characterization of putative pluripotential embryonic stem cells from preimplantation rabbit embryos" Mol. Reprod. Dev. 36:424-433 (1993).

Iannaccone et al. "Pluripotent embryonic stem cells from rat are capable of producing chimeras" Dev. Biol. 163:288-292 (1994).

Meinecke-Tillmann. "Experiments on the establishment in culture of pluripotential cell lines from sheep, goat, and pig embryos" In Seventh Scientific Meeting of the A.E.T.E. Cambridge, pp. 178 (1991).

Notarianni et al. "Derivation of pluripotent, embryonic cell lines from the pig and sheep" J. Reprod. Fert., Suppl. 43:255-260 (1991).

Notarianni et al. "Maintenance and differentiation in culture of the pluripotential embryonic cell lines from pig blastocysts" J. Reprod. Fert., Suppl. 41:51-56 (1990).

Wheeler. "Development and validation of swine embryonic stem cells: a Review" Reprod. Fertil. Dev. 6:563-568 (1994).

Williamson. "Mapping of the prion protein using recombinant antibodies" J. Virol. 72:9413-9418 (1998).

Aguzzi, A. et al., "Transgenic and Gene Disruption Techniques in the Study of Neurocarcinogenesis", *GLIA*, 1995, 15:348-361.

Charreau, B. et al., "Transgenesis in Rats: Technical Aspects and Models", *Transgenic Research*, 1996, 5:223-234.

Hammer, R. et al., "Production of Transgenic Rabbits, Sheep and Pigs by Microinjection", *Nature*, 1985, 315:680-683.

Robl, J. et al., "Part III: Production of Trangenic Laboratory and Domestic Animal Species (Chapters 9-12)", *Transgenic Animal Technology: A Laboratory Handbook*, 1994.

Claesson et al. (1994). "Antibodies directed against monomorphic and evolutionary conserved self epitopes may be generated in 'knock-out' mice. Development of monoclonal antibodies directed against monomorphic MHC class I determinants," *Scandinavian Journal of Immunology* 40(2):257-264.

Roes et al. (1995). "Mouse anti-mouse IgD monoclonal antibodies generated in IgD-deficient mice," *Journal of Immunological Methods* 183(2):231-237.

Brown, J. et al., (1991) "The gene encoding the stem cell antigen, CD34, is conserved in mouse and expressed in haemopoietic progenitor cell lines, brain, and embryonic fibroblasts" *International Immunology* 3(2):175-184.

Castrop, J. et al., (1995) "Circumvention of tolerance for the nuclear T cell protein TCF-1 by immunization of TCF-1 knock-out mice" *Immunobiol.* 193:281-287.

Claesson, M.H. et al., (1994) "Antibodies directed against monomorphic and evolutionary conserved self epitopes may be generated in 'knock-out' mice. Development of monoclonal antibodies directed against monomorphic MHC class I determinants" *Scand. J. Immunol.*40:257-264.

Oosterwegel, M. et al., (May 1991) "Cloning of murine TCF-1, a T cell-specific transcription factor interacting with functional motifs in the CD3-ϵ and T cell receptor α enhancers" *J. Exp. Med.* 173:1133-1142.

Roes, J. and Rajewsky, K. (1991) "Cell autonomous expression of IgD is not essential for the maturation of conventional B cells" *International Immunology* 3(12):1367-1371.

Roes, J. and Rajewsky, K. (Jan. 1993) "Immunoglobulin D (IgD)-deficient mice reveal an auxiliary receptor function for IgD in antigen-mediated recruitment of B cells" *Journal of Experimental medicine* 177:45-55.

Sugimoto, K. et al., (1992) "An antigenic determinant on human centromere protein B (CENP-B) available for production of human-specific anticentromere antibodies in mouse" *Cell Structure and Function* 17:129-138.

Valdez, B.C. et al., (1992) "A region of antisense RNA from human p120 cDNA with high homology to mouse p120 cDNA inhibits NIH 3T3 proliferation" *Cancer Research* 52:5681-5686.

Yorifuji, T. et al., (1991) "Molecular cloning and sequence analysis of the murine cDNA for the cystic fibrosis transmembrane conductance regulator" *Genomics* 10:547-550.

* cited by examiner

Titration of δ1.3 and δ3.5 AMAB's on mouse spleen cells

Double staining of mouse spleen cells
with anti-IgM and anti-IgD antibodies separation of mouse spleen cells using anti-IgD antibodies conjugated to superparamagnetic colloidal particles

ANTIBODIES AGAINST EPITOPES WITH HOMOLOGY TO SELF ANTIGENS, METHODS OF PREPARATION AND APPLICATIONS THEREOF

TECHNICAL FIELD

This invention relates to methods of obtaining autologous monoclonal antibodies (AMAB) to self-antigens or homologs thereof, and the use of these antibodies in the analysis of cell populations and in cell separation techniques.

BACKGROUND ART

Antibodies have proven useful in medical applications for both diagnosis and therapy, and in biotechnology applications including cell separation. More generally, their high degree of binding specificity facilitates their use in the identification and localization of any compound to which antibodies can be generated in conjunction with techniques as varied as electron microscopy and enzyme linked immunosorbent assays.

Antibodies are comprised of both heavy and light chain polypeptides joined by interchain disulfide bonds and other intramolecular interactions. An individual heavy chain is paired with an individual light chain by these disulfide bonds. Of the different classes or isotypes of antibodies, three isotypes (IgD, IgE, and IgG) are comprised of two identical heavy chain/light chain pairs joined by a disulfide bond, and the remaining two isotypes (IgA and IgM) are comprised of more complicated polymers of identical heavy chain/light chain pairs. Each chain contains a constant region and a variable region. The constant regions are peculiar to the animal that generates the antibody and the specific isotype of antibody, while the variable regions conform to the structure of the epitope to which the antibody binds.

The term "antigen" is used herein to refer to a substance, whether an entire molecule or a domain within a molecule, which is capable of eliciting production of antibodies with binding specificity to that substance. Further, the term antigen is applied herein to substances, which in wild type host organisms would not elicit antibody production by virtue of self-recognition, but can elicit such a response in a host animal with the appropriate genetic engineering.

The term "epitope" is used herein to refer to the discrete, three-dimensional sites on an antigen, which are recognized by B lymphocytes. Epitopes are the immunologically active regions on a complex antigen, the regions that actually bind to a B-cell receptor, and that are actually bound by the resulting antibody molecules that are produced by the B-cell. Antigens generally contain at least one epitope and usually more than one epitope. Epitopes on protein antigens can be linear or non-linear. Linear epitopes are those comprised of contiguous amino acid residues in the amino acid sequence of a protein. Linear epitopes may or may not require conformational folding to form the native three-dimensional structure and elicit an immune response that produces antibodies with binding specificity to the antigen. Non-linear epitopes are comprised of non-contiguous amino acid residues. Thus, non-linear epitopes always require some degree of protein folding to bring the requisite amino acid residues into the proximity of one another to form the native three-dimensional structure and elicit an immune response that produces antibodies with binding specificity to the antigen.

The term "self" is used herein to describe antigens or epitopes which would not be recognized or be only poorly recognized by the B-cell receptors of a wild type member of the host species, by virtue of being included among the substances which are normally biosynthesized by the host species, or to which the host species is normally exposed. Such substances induce tolerance of the host immune system and the host is said to be "tolerized" to the substances.

The vertebrate immune system is able to discriminate between self-antigens and foreign antigens, mounting an antibody-mediated immune response to the latter and not the former. The antibody response is mediated by the B cells. Variable-region gene rearrangements occur in an ordered sequence during B-cell maturation in the bone marrow. At the end of this process, each B cell contains a single, functional variable-region DNA sequence encoding an immunoglobulin heavy chain and a single, functional variable-region DNA sequence encoding an immunoglobulin light chain. This process leads to the generation of mature, immunocompetent B cells each of which is antigenically committed to a single epitope. In a process that is not yet understood, immunologic tolerance to "self" components is accomplished by the selective ablation of B cells with variable regions that are antigenically committed to self-epitopes. This self-tolerance precludes production of antibodies specific for antigens or epitopes that are synthesized by a host vertebrate. Thus, only antigens that contain epitopes which are recognized as foreign by the host can be used to generate antibodies.

When the self and foreign epitopes are structurally similar, or "homologous", the host immune response is weaker; thus it is virtually impossible to obtain antibodies with high affinity to such epitopes. As a result, it is extremely difficult to generate antibodies to highly conserved domains of proteins (e.g. N-CAM, cytokines, and immunoglobulins), because animals that share the conserved domains fail to recognize them as foreign. While antibodies to self-antigens are produced as a result of certain autoimmune diseases, these antibodies have binding specificities to a highly restricted set of self-antigens which cannot be manipulated artificially and generally have low binding affinities. Thus, animals with autoimmune diseases are not widely useful in the production of antibodies with binding specificity to self-antigens.

In mice, allogeneic differences between strains have allowed the production of mouse anti-mouse antibodies specific for proteins of which such allogeneic differences have been produced. Kessler et al. (1979) *J. Immunol.* 123:2772–2778; Reif and Allen (1964) *J. Exp. Med.* 120: 413–433; Marshak-Rothstein (1979) *J. Immunol.* 122:2491–2497; and Oi and Herzenberg (1979) *Molec. Immunol.* 16:1005–1017. Initially, polyclonal antisera and then monoclonal antibodies specific for T cell surface proteins and mouse IgD antibodies were obtained in this manner. These antibodies, however, only recognize the gene product of particular mouse strains. These antibodies can only recognize those/epitopes/which are not structurally homologous to the self-antigens of the antibody-producing host. Additionally, the epitopes against which these antibodies can be obtained are limited to the differences between the strains and availability of allotypic strains themselves and thus have little practical utility.

Numerous methods have been formulated to analyze and sort populations of cells including, but not limited to, fluorescence activated cell sorting (FACS), magnetic separation (using magnetic bead-conjugated antibodies) and other methods reliant upon antibody affinity to particular cell surface proteins known as "markers". Such approaches to cell analysis and separation are especially useful for the determination of cell lineages, the isolation of cells which are capable of synthesizing a particular product, and the treatment of various disease conditions with specific cell types. For example, highly purified hematopoietic stem cells are essential for hematopoietic engraftment including, but not limited to, cancer patients and transplantation of other organs in association with hematopoietic engraftment. Isolated cell populations are also important targets for gene therapy in the treatment of genetic disorders, AIDS and various forms of cancer. Thus, there have been numerous efforts made toward isolating particular varieties of cells in substantially pure or pure form. In instances such as isolation of stem cells, efficient purification of cells of such low concentration in the body requires antibodies which recognize and bind to stem cell specific markers with high specificity. Such antibodies are difficult to obtain due to the homology between human and murine stem cell markers.

SUMMARY OF THE INVENTION

This invention provides novel methods of obtaining autologous monoclonal antibodies (AMABs) to a self-antigen or homolog thereof. The method includes obtaining a genetically engineered host animal that does not biosynthesize or synthesizes an altered form of at least one epitope within the self-antigen and utilizing the host lack of self-tolerance to the at least one epitope to produce antibodies specific to that antigen. The invention also encompasses the antibodies or any functional derivative thereof produced by the method. The invention further encompasses methods of isolating cells comprising utilizing the antibodies obtained by the method described herein which are specific to a cell surface antigen.

MODES OF CARRYING OUT THE INVENTION

Figure 1:
FIG. 1 is a picture depicting anti-IgD antibody staining of mouse spleen tissue in B cell rich areas.

The invention provides novel methods of obtaining AMABs which have binding specificity to self-antigens or homologs thereof. The invention provides a means for overcoming the limitation on producing AMABs to antigens that the host recognizes as self, as well as a method for obtaining "targeted antibodies," that is, AMABs with binding specificity to known, particular and extremely precise epitopes. The invention also allows for obtaining AMABs to biological molecules, or epitopes thereof, considered essential for growth and development. As discussed more fully herein, targeted genetic replacement allows for production of functional equivalents of the molecules and thus allows sufficient growth and development of the animal to produce antibodies.

The term "homolog" is used herein to refer to an antigen with a structure that is so similar to an antigen produced by the host animal, a "self-antigen", as to preclude or seriously hinder the production of antibodies to the homolog. The phrase "self-antigen or homolog thereof" is used herein to signify that the invention is not directed solely to obtaining AMABs with binding specificity to self-antigens, but rather the invention is directed to obtaining AMABs to any compound with such a high degree of structural similarity to a self-antigen, that the homolog is sufficiently recognized as self that the host animal does not produce an adequate antibody-mediated immune response. An adequate antibody-mediated immune response is one in which either AMABs are not obtained or, if produced, they do not have high affinity for the antigen.

The term "target antigen" is used herein to refer to the composition to which the host animal is exposed and against which an immune response is generated. The "target antigen epitope" is a region on the target antigen to which the AMABs bind.

The term "immune response" is used herein to refer to the production of AMABs by B cells. These antibodies bind to a particular antigen regardless of whether they effect a change in the antigen such as providing immunity to a disease causing agent. The AMABs may be associated with the B cell surface and may also be freely circulating.

The term "structurally non-homologous" is used herein as a description to compare self-antigens with antigens biosynthesized by host animals as a result of genetic engineering. Two antigens are structurally non-homologous, when an antibody can be generated that binds to one and not the other. Structurally non-homologous means that there is some structural difference, perhaps slight, between two or more antigens. The structurally non-homologous difference between two antigens can be as small as a single amino acid difference, or the presence or absence of a methyl group.

The term "functionally equivalent" is used herein as a description to compare self-antigens and target antigens biosynthesized by host animals as a result of genetic engineering. In many cases, disrupting synthesis of a self-antigen can prove lethal, reduce survivorship or the overall health of genetically engineered host animals so as to interfere with obtaining antibodies. Thus, as described herein, genetic engineering can be used to eliminate the biosynthesis of a self-antigen and cause the production of another, functionally equivalent antigen. This functionally equivalent antigen exerts a sufficient amount of the self-antigen function to compensate for the deleterious elimination of the self-antigen by improving the rate of survivorship, overall health or immunocompetence of the host animal to the extent that AMABs may be obtained. As used herein, functionally equivalent antigens are understood to be structurally non-homologous.

The term "biosynthetic repertoire" is used herein to refer to the sum total of all of the compounds biosynthesized by a given host animal.

The term "wild type" is used herein to describe individuals of the host species and strains that have not been subjected to genetic engineering relating to the target antigen and are not descended from such a genetically engineered organism.

The term "genetically engineered" is used to describe animals that have had one or more genes directly altered or eliminated so as to prevent or alter synthesis of a particular antigen or set of antigens. Such alteration or elimination is at the genetic level, for instance by specific genetic knockout and replacement. Genetic engineering of the target antigen is generally limited to the extent that antibodies can be obtained with enhanced binding specificity to at least one epitope on the antigen or set of antigens, as described herein. The term "genetically engineered" is also applied to the progeny of the originally altered animals.

The term "domain" is used herein to refer to any region or portion of an antigen, including the whole antigen, any portion which is less than the whole antigen, or any region which is more than the whole antigen by virtue of the addition of components which may serve to mask at least one epitope.

In one embodiment of the invention, the host animal is genetically engineered so that it does not synthesize a particular self-antigen. When the genetically modified host is immunized with the self-antigen or a homolog thereof, the host immune system does not recognize the antigen as self, and is thus able to produce an antibody-mediated immune response from which AMABs can be obtained. Methods of obtaining such "knock-out" mutants are known in the art and are described for instance, in Mansour et al. (1998 *Nature* 336:348–352. As with most genetically engineered host animals used herein, breeding may be used to achieve a homozygous mutant or to obtain multiply genetically engineered host animals. Thus, the genetic modification to the host can ultimately be acquired through germ-line transmission.

Progeny of the genetically engineered mice are also encompassed by the invention. Any other method known in the art of creating transgenic animals is suitable for use herein. Suitable methods include, but are not limited to, those described by Kitamura et al. (1991) Nature 350: 423–426; Shinkai et al. (1993) Science 259:822–825; and Komori et al. (1993) Science 261:1171–1175. Briefly, in the case of self-antigens of the immune system, embryonic stem (ES) cells homozygous for the gene modification can be implanted into blastocysts of immunodeficient mice such as RAG-deficient mice. The reconstituted animal will, in many cases, lack the immune deficient phenotype and contain the gene modification in its lymphocytes.

In another embodiment of the invention, the host animal is genetically engineered such that the synthesis of a particular self-antigen is replaced by the synthesis of a functionally equivalent antigen. Thus, antibodies can be obtained for antigens the elimination of which would prove lethal, drastically reduce survivorship, or otherwise hamper efforts to obtain antibodies.

The self-antigen that is eliminated from the biosynthetic repertoire of the host can be any compound, domain, or epitope thereof, that is normally synthesized by a wild type member of the host species. The antibodies obtained by the invention can be directed to any antigen, including but not limited to, proteins, carbohydrates, lipids, nucleic acids, enzyme cofactors or any naturally-occurring aggregates or covalently-linked combinations thereof, or any phosphorylated or sulfonated species thereof. For these embodiments of the invention, the host can be genetically engineered in any way such that the biosynthesis of the antigen is eliminated or altered. For example, knocking out the expression of a particular enzyme that is involved in the biosynthesis of the antigen can result in nonproduction of the antigen or the production of a functionally equivalent antigen. Such enzymes include, but are not limited to, enzymes involved in the polymerization and attachment of carbohydrates, phosphate groups, lipids, sulfur-containing groups to proteins. Any of these could be eliminated, resulting in the elimination or change in structure of the compounds that are covalently attached to proteins, as in the synthesis of glycoproteins. Thus, antibodies with binding specificity to particular self-glycoproteins or carbohydrate structures on glycoproteins can be obtained by the methods of the invention.

More global methods of eliminating or changing production of antigens may be utilized. These methods include, but are not limited to, eliminating synthesis of particular genes or gene families and eliminating particular cell types. Examples of suitable genes and gene families include those regulated by the presence of particular factors such as steroids or cytokines or genes which are expressed in a cell type specific manner. An example of such a cell type is brown fat cells.

In the preferred embodiment of the invention, the antigen is a protein. A knockout mutation for a protein could involve preventing the synthesis of the entire protein (by removing the entire gene or by altering transcriptional or translational control elements) or eliminating the synthesis of just one antigenic domain, while allowing the remaining portion of the protein to be synthesized normally. In the case of a protein antigen, the replacement of the self-antigen with a functionally equivalent antigen, entails at least three distinct types of replacements although any formal replacement known in the art is suitable for use herein.

First, the gene encoding the self-antigen can be replaced by a recombinant gene derived from the gene encoding the self-antigen. The gene encoding the protein is altered such that an antigenic region is deleted, replaced by an alternative amino acid sequence, or masked by the addition of a novel amino acid sequence. Thus, in the modification of a self-protein antigen, the genetically engineered elimination of the antigen can be as minor as the addition, elimination or substitution of a single amino acid. Importantly, such small changes in the structure of the self-protein antigen allow AMABs to extremely precise epitopes to be obtained without severely disrupting the function of the self-antigen. A single amino acid change in a suitable domain would result in AMABs to epitopes that include the single amino acid.

Second, the gene encoding the self-antigen can be replaced by the gene that encodes a homologous protein obtained from an organism that is related to the host species, such that the encoded protein is functionally equivalent but at least partially antigenically non-equivalent. Closely related species usually have a high degree of sequence homology for the same protein, typically greater than 90%. Thus this strategy is ideal for practicing the invention in cases in which expression of the antigen is critical to the health of the organism, and AMABs with binding specificity to a small number of epitopes is desired. This strategy can also be practiced by replacing only a region of the gene encoding the self-antigen with the corresponding region of the gene encoding the same antigen from a related species.

Third, the gene encoding the self-antigen can be replaced by a gene encoding a protein that is known to have the same or a similar function, but is structurally non-homologous. This strategy is particularly useful where expression of the antigen is critical to the health of the organism and AMABs with binding specificity to particular epitopes is not required.

Examples of the protein antigens to which the AMABs obtained by the invention can have binding specificity, include, but are not limited to, cell surface antigens, including, but not limited to, adhesion molecules, MHC class I and class II molecules, integrin, cytokines, selecting, cytokine receptors and immunoglobulins.

The invention can be practiced using any non-human vertebrate host, including fish, reptiles, amphibians, birds, and mammals. However, the host is almost always a mammal and usually belongs to an order including, but not limited to, rodentia, lagomorpha, primates, carnivora, perissodactyla and artiodactyla. Preferably the host is murine and most preferably a mouse.

Methods of making AMABs are known in the art and are not described in detail herein. Any method known in the art of monoclonal antibody production can be used herein. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the AMABs are obtained from immortalized antibody-producing hybridoma cells. These hybridomas can be produced by fusing B lymphocytes, preferably isolated from the immunized host spleen, with compatible immortalized cells, preferably a B cell myeloma.

The invention further encompasses compositions of matter comprising the AMABs obtained by the methods described herein. As used herein, the terms "AMAB(s)," "antibody" or "antibodies" include the entire antibody and antibody fragments containing functional portions thereof. The term "AMABs" includes any monospecific compound comprised of a sufficient portion of the light chain variable region and/or the heavy chain variable region to effect binding to the epitope to which the whole antibody has binding specificity. The fragments may include the variable region of at least one heavy or light chain immunoglobulin polypeptide, and include, but are not limited to, Fab fragments, Fab2 fragments, and Fv fragments.

In addition, the monospecific domains may be attached by any method known in the art to another suitable molecule. The attachment may be, for instance, chemical or by genetic engineering. The AMABs may be produced by any recombinant means known in the art. Such recombinant AMABs include, but are not limited to, fragments produced in bacteria and AMABs in which the majority of the constant regions have been replaced by human antibody constant regions. In addition, such "humanized" AMABs may be obtained by breeding the genetically engineered host vertebrates described herein with a compatible transgenic animal that expresses functional human Ig loci in place of the wild type Ig loci. For a discussion of transgenic animals expressing human Ig loci, see WIPO publication number WO 91/10741 and Rajewsky et al. DE P4228162.8. With successive crosses, host animals that do not express a particular self-antigen, but do express humanized Ig proteins can be obtained. When such animals are immunized they will produce humanized or partly humanized AMABs to particular self-antigens. Such humanized AMABs are preferred for use in therapeutic indications.

The AMABs can be conjugated to other compounds including, but not limited to, enzymes, magnetic beads, colloidal magnetic beads, haptens, fluorochromes, metal compounds, radioactive compounds, drugs or haptens. The enzymes that can be conjugated to the AMABs include, but are not limited to, alkaline phosphatase, peroxidase, urease and β-galactosidase. The fluorochromes that can be conjugated to the AMABs include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P. *Molecular Probes: Handbook of Fluorescent Probes and Research Chemicals* (1992–1994). The metal compounds that can be conjugated to the AMABs include, but are not limited to, ferritin, colloidal gold, and, particularly, colloidal superparamagnetic beads. The haptens that can be conjugated to the AMABs include, but are not limited to, biotin, digoxygenin, oxazalone, and nitrophenol. The radioactive compounds that can be conjugated or incorporated into the AMABs are known to the art, and include, but are not limited, to technetium 99m ($^{99}$TC), $^{125}$I and amino acids comprising any radionuclides, including, but not limited to, $^{14}$C, $^{3}$H and $^{35}$S. Any drug known in the art that can be conjugated to protein by any method known in the art is suitable for use in the present invention. Such drugs can be conjugated to the AMABs for highly specific delivery to the target molecule.

The invention further provides methods of using the AMABs, including but not limited to, immunoassays and separating cells. Suitable immunoassays are known in the art and need not be described in detail herein. These include, but are not limited to, ELISAs and RIAs. Methods of cell separation include, but are not limited to, separation based on secretion of molecules and separation based on cell surface molecules. Methods of separating cells based on secretion of molecules are described in Ser. No. 07/965,934 and International Application No. PCT/US93/10126. Methods for separating cells based on specific cell surface markers generally include the steps of obtaining the AMABs by the methods described herein, contacting the AMABs to a heterogeneous population of cells, and performing a cell separation technique based on the affinity of the AMABs for the cell surface antigen. Any method known in the art may be employed to separate or isolate the cells by initially removing cells with particular cell surface antigens or of particular lineages.

AMABs are particularly useful for identifying markers associated with particular cell lineages and/or stages of differentiation. The AMABs may be attached directly or indirectly to a solid support to allow for separation. The separation techniques employed should maximize the retention of viability of the fraction to be collected. Various techniques of different efficacy may be employed to obtain separations. Such separations are where up to 10%, usually not more than about 5%, preferably not more than about 1%, of the total cells present not having the marker may remain with the cell population to be retained. The particular technique employed will depend upon efficiency of separation, cytotoxicity of the methodology, ease and speed of performance, and necessity for sophisticated equipment and/or technical skill.

Procedures for cell separation include, but are not limited to, magnetic separation using antibodies linked to colloidal magnetic particles, affinity chromatography and cytotoxic agents joined to a monoclonal antibody or used in conjunction with any antibody-dependent separation techniques known in the art. In addition, cells may be separated by "panning" with antibody attached to a solid matrix, e.g., a plate. Fluorescence activated cell sorting (FACS) may also be used and may have varying degrees of sophistication, including, but not limited to, a plurality of color channels, low angle and obtuse light scattering detecting channels, and impedance channels. Any antibody-dependent separation technique known in the art may be used in conjunction with both positive and negative separation techniques that rely on the physical properties of the cell rather than antibody affinity, including, but not limited to, elutriation and density gradient centrifugation.

Methods to separate cells are commercially available from Dynal, Oslo Norway, Cellpro, Seattle, or Advanced Magnetics, Boston. For example, autologous monoclonal antibodies can be directly coupled to magnetic polystyrene particles like Dynal M 450 or similar magnetic particles and used, e.g., for cell separation. Alternatively, antibodies can be biotinylated or conjugated with digoxigenin and used in conjunction with avidin or anti-digoxigenin coated affinity columns like SEPARATE LC (Cellpro). In a preferred embodiment, however, autologous monoclonal antibodies are used in conjunction with colloidal superparamagnetic microparticles having an organic coating by, e.g., polysaccharides. Miltenyi et al. (1990) Cytometry 11:231–238. These particles can be used having a size of 10 to 200 nm, preferably between 40 and 100 nm, and can be either directly conjugated to autologous antibodies or used in combination with anti-immunoglobulin, avidin, or anti-hapten-specific microbeads. Polysaccharide-coated superparamagnetic particles are commercially available from Miltenyi Biotec GmbH, Germany.

One procedure which may be used is first incubating the cells for a short period of time at reduced temperatures, generally about 4° C., with saturating levels of AMABs specific for a particular cell surface antigen, and then washing the cells with PBS and a fetal calf serum (FCS) cushion. The cells may then be suspended in a buffer medium as described above and separated on the basis of the AMABs for the particular determinants, using various protein(s) specific for the AMABs or AMAB-antigen complex.

The AMABs may be conjugated with markers, including, but not limited to, magnetic beads, which allow for direct separation, biotin, which can be removed with avidin or streptavidin bound to a support, digoxigenin detected by anti-digoxigenin antibodies and fluorochromes, which can be used with a FACS, or the like, to allow for ease of separation of the particular cell type. Any technique may be employed which is not unduly detrimental to the viability of the remaining cells.

After substantial enrichment of the cells containing the cell surface antigen, generally by at least about 50%, preferably at least about 70%, the cells may then be separated by a FACS or other methodology known to the art. Multi-color analyses may be employed, by a variety of the methods including, but not limited to, FACS and fluorescence microscopy. The cells may be separated on the basis of the level of staining for the particular antigens.

The invention further encompasses obtaining AMABs to self-antigens which are receptors by the method described herein and using such AMABs as pharmaceutical agents, wherein the AMABs demonstrate efficacy as receptor agonists or antagonists.

The following examples are meant to illustrate, but not limit, the invention.

EXAMPLE 1

Gene Targeting

Gene targeting of the Cδ gene was performed as described by Roes and Rajewsky (1993) *J. Exp. Med.* 177:45–55; and Roes and Rajewsky (1991) *Int. Immunol.* 3:1367–1371. Briefly, a total of $10^8$ E14-1 ES cells were transfected with the targeting vector designed to replace a large part of the Cδ1 exon and to insert frameshift mutations in Cδ3 by filling in restriction sites present in this exon. The introduction of the mutations into the germ-line resulted in functional inactivation of both δ chain Ig domain exons. This was considered important to exclude the possibility of expression of a truncated δH chain that could compete with μ for L chains and be secreted. The presence of the frameshift in the mouse germ-line was indicated by an NheI restriction site resulting from filling in the HindIII site in Cδ3. The Cδ2 exon is a pseudoexon due to a nonfunctional splice acceptor.

Colonies surviving selection were analyzed by PCR, and positive clones were further analyzed by Southern blotting to confirm the structure of the targeted locus. Homologous recombinants were obtained at a frequency of 1/17 double-resistant or 1/103 G418-resistant clones. Restriction maps of wild-type and mutated Cδ loci as well as restriction analysis of HindIII-digested genomic DNA from five individual candidate recombinants and control cells are shown. A homologous recombination event would result in a 4.4- or 6.0-kb band in addition to the 3.8-kb germ-line band, depending on the presence or absence of the frame shift mutation in Cδ3 that results in loss of the HindIII site. 9 of 10 homologous recombinant clones showed the 6.0-kb fragment, indicating that the breakpoint of recombination was located 3' of the Cδ3 exon. Thus, the Cδ1 and Cδ3 exons were rendered nonfunctional in these clones. One clone retained the HindIII restriction site in the Cδ3 exon, resulting in a diagnostic restriction fragment of 4.4 kb. The structure of the targeted locus was confirmed using a variety of other probes and restriction enzymes. Southern blot analysis was performed as described by Sambrook, Fritsch, and Maniatis, *Molecular Cloning, A Laboratory Manual, 2nd ed.* Cold Spring Harbor Laboratory, NY (1989).

EXAMPLE 2

Generation of IgD-Deficient Mice

The generation of IgD-deficient mice was performed as described by Roes and Rajewsky (1993) Briefly, the strategy of Cδ gene inactivation and the screening procedure for positive clones was as described in Example 1. Targeted ES cell clones were injected into blastocysts isolated from C57BL/6 mice and transferred to (C57BL/6×BALB/c) fosters. Male chimeric offspring were mated with C57BL/6 females for germ-line transmission of the δT mutation. Offspring derived from ES cells were identified by coat color and analyzed for the presence of the mutation, which was called δT, by Southern blotting or phenotypically, by flow cytometry. Homozygous mutant mice (δT/δT) were obtained by the interbreeding of heterozygous offspring.

EXAMPLE 3

Northern Blot Analysis of Putative (δT/δT) Mutant Mice

The northern blot analysis of putative (δT/δT) mutant mice was performed as described by Roes and Rajewsky (1993). Briefly, the δT mutation results in functional inactivation of both exons encoding Ig domains of the H chain. The transmembrane and the hinge region exons, however, remain intact and potentially functional. To exclude the possibility that aberrant splicing of precursor RNA encompassing both the Cμ and the Cδ genes resulted in the generation of a significant amount of chimeric Ig transcripts encoding the extracellular domains of the Cμ gene and the transmembrane and cytoplasmic portion of Cδ, poly(A)$^+$ RNA isolated from spleens of homozygous mutant (δT/δT) and wild-type mice was analyzed by Northern blotting. mRNA containing Cμ exons spliced to the Cδ transmembrane exon would be larger than the normal Cμ transcripts of 2.4 (μs) or 2.7 kb (μm), because the 3'-untranslated region of the δ message is 600-bp longer than that of the μ message.

Hybridization of splenic poly(A)+ RNA of homozygous mutant mice with a Cδ transmembrane-specific probe reveals bands of 4.8-, 4.0-, 3.8-, and 3.0-kb. However, none of these bands hybridized with the Cμ-specific probe. The detection limit of the two probes was similar within a factor of two ($1.2 \times 10^6$ copies for the Cμ and $0.6 \times 10^6$ for the δm probe) as judged by the signals obtained from hybridization to standard plasmid DNA. The Cμ probe is a cDNA fragment of 1 kb with complete match to the mRNA and the standard plasmid, whereas the δm probe hybridizes to the mRNA over a stretch of only 480 bp, but 700 bp on the plasmid standard because it contains the δm1/m2 intron. Consequently, a mRNA representing Cμ exons spliced to the δm exons, if detected with the δm probe, should also be revealed with the Cμ probe. Because the 3.0-, 3.8-, 4.0-, and 4.8-kb bands are clearly above the δm probe detection limit, they should, if containing Cμ sequences, also be detected with the Cμ probe. This, however, is not the case.

Furthermore, sequential hybridization of the same blot with a $neo^+$ gene and a probe specific for the $Cδ_3$ exon demonstrated that the 3.8-, 4.0-, and 4.8-kb bands also contain sequences derived from the $neo^+$ gene, indicating that they represent aberrant splice products. The 3.0-kb band hybridized with the probe specific for the Cδ3 exon which is nonfunctional in the targeted allele because of frame shift mutations described in Example 1. In addition, with the $neo^+$ probe, mRNA of 2.4 kb, which did not hybridize with the δm probe, was also detected. Low abundance mRNAs of 1.6 and 2.0 kb hybridizing with a Cδm-specific probe are detectable in 10 μg poly(A)$^+$ RNA from both normal and mutant mice. These mRNAs, however, are smaller than the normal Cμ message and therefore, unlikely to encode a functional Ig molecule.

Taken together, mRNA species representing potentially functional chimeric μ/δ molecules were undetectable in Northern blots using as much as 10 μg of splenic poly(A)$^+$ RNA of δT/δT mice. Because mRNA encoding the δH chain can be detected with the Cδm-specific probe in as little as 300 ng of poly(A)$^+$ RNA of spleens of normal mice, a putative mRNA encoding the extracellular domains of μ and the transmembrane portion of δ would be at least 30-fold less abundant than δH chain message in normal mice, if it exists at all. Thus, mRNA potentially able to encode an IgD-like molecule is undetectable in homozygous mutant mice (δT/δT) by northern blot analysis.

EXAMPLE 4

Production of Mouse-anti-Mouse-IgD Monoclonal Antibodies

IgD-deficient mice were generated by gene-targeting as described in Examples 1 and 2. One animal obtained thereby was immunized intraperitoneally (i.p.) with mouse monoclonal antibody of class IgD (267.7δ "a" allotype) precipitated in alum.

After 6 weeks, the animal was boosted i.p. with soluble B1-8 of "b" allotype to obtain monoclonal antibodies recognizing both allotypes.

After 3 days, spleen cells of the immunized mouse were fused with X63 Ag8.6.5.3 using a standard PEG fusion protocol. Hybrids were directly cloned into eight 96-well plates and selected using HAT selective medium. Hybridomas obtained were screened for production of anti-IgD antibodies by ELISA using plates coated with B1-8 (IgD), BSA (bovine serum albumin), 267.7 (IgD), R33-24-12 (anti-IgM) and developed using R33-18-10.1-Biotin (rat anti-mouse Kappa) and R33-60-Biotin (anti-IgM) antibodies. Seventeen clones showed reactivity to B1-8 (IgD$^b$), thirteen of these showed reactivity to 267.7 (IgD$^a$), one of these was of class IgM. Two other clones showed reactivity to IgM but not to IgD. Hybridomas were further characterized for relative binding affinity and isotype. Fifteen of 21 clones tested showed IgG1 isotype. Additionally, clones were characterized for binding to trypsin-treated and untreated mouse spleen cells using biotinylated anti-mouse IgG1 and streptavidin-phycoerythrin. Trypsin cuts surface IgD and allows localization of the epitope on the IgD molecules.

Three clones of highest affinity and IgG1 isotype (δ1.2, δ1.3 and δ3.5) were used for further experiments. Several mg of purified AMABs produced by these clones were produced using roller bottles according to standard methods. 16 clones were tested in a staining assay by incubating mouse spleen cells with culture supernatant. Bound anti-IgD AMAB was detected with a biotinylated anti-mouse-IgG1 and revealed by Streptavidin-PE.

EXAMPLE 5

IgD AMAB Staining of Mouse Spleen Tissue in B Cell Rich Areas

Frozen spleen sections from a C57BL/6 Mouse were stained with biotinylated mouse anti-mouse IgD AMAB δ1.3 prepared as described in Example 4 and biotinylated using Pierce NHS biotin according to the instructions of the supplier. Staining patterns were developed with peroxidase coupled to Streptavidin using an AEC Staining Kit from Sigma as per the manufacturer's instructions. The results obtained are depicted in FIG. 1. The staining pattern is identical to that seen for polyclonal goat anti-mouse IgD antisera, demonstrating that the IgD AMABs obtained by the invention have binding specificity to the desired self-antigen.

EXAMPLE 6

Figure 2:
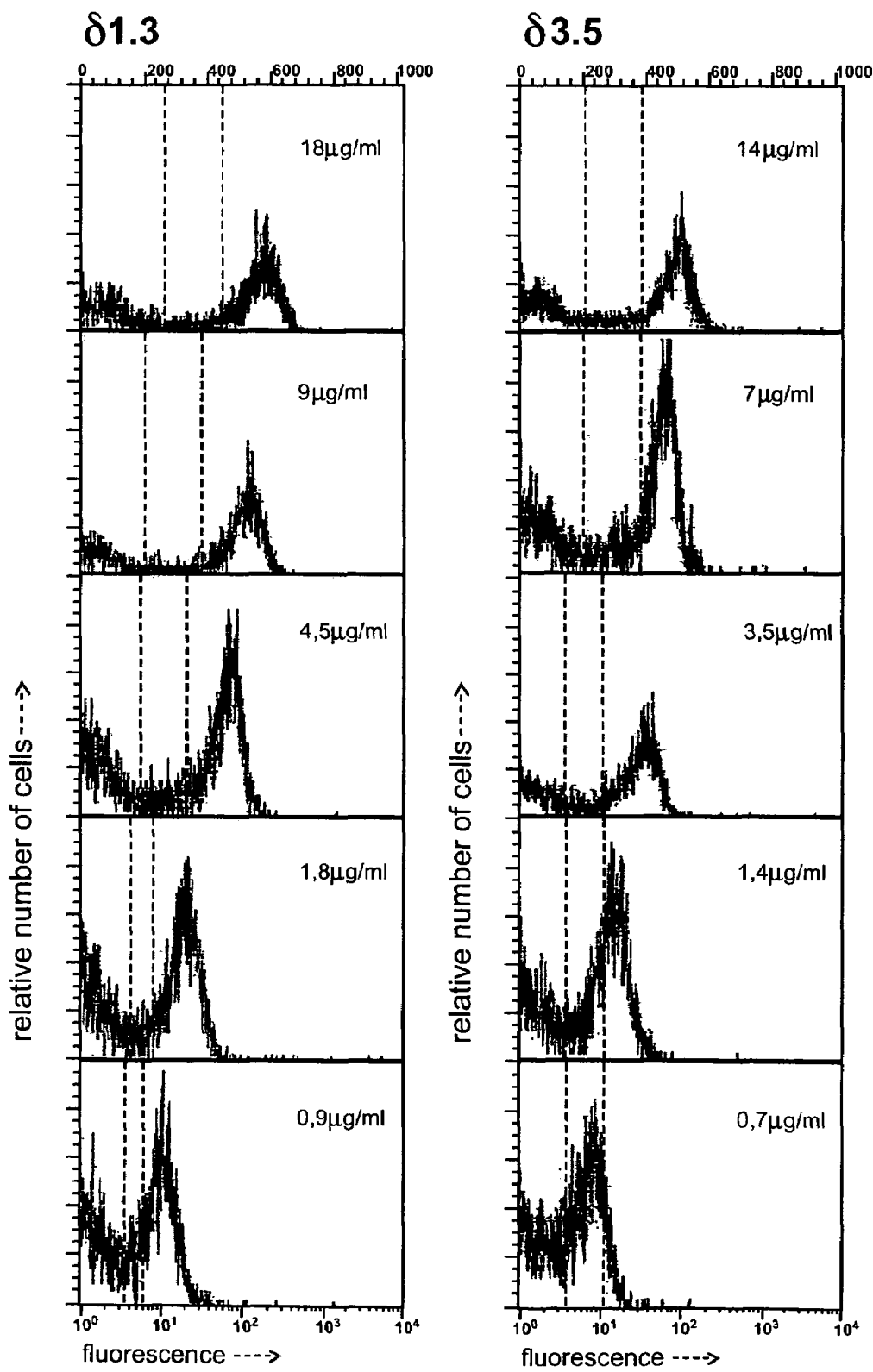
FIG. 2 depicts the results of titration of δ1.3 and δ3.5 AMABs on mouse spleen cells.

Conjugation of Antibodies to Fluorescein and Staining of Spleen Cells Under Different Concentrations 0.5 mg purified AMAB (δ1.3 and δ3.5) each obtained from Example 4 were rebuffered into 1.5 ml 0.1 M $NaHCO_3$ and reacted for 1 hour with 15 μl carboxylfluorescein-hydroxy-succinimide ester (Boehringer Mannheim) dissolved in DMSO (1 mg/ml). Unbound fluorescein was removed by gel filtration. The F/P ratio was determined to be approximately 3–3.5 for both conjugates. One million mouse spleen cells were incubated for 15 minutes with the different dilutions of the conjugated AMABs shown in FIG. 2 and analyzed by Flow cytometry. The results obtained are depicted in FIG. 2. The data show that concentrations as low as 1 μg/ml are sufficient for detecting IgD-positive cells and that the AMABs have high affinity.

EXAMPLE 7

Two-Color Staining of Mouse Spleen Cells

Spleen cells obtained from a B6×129 mouse were stained with the fluorescein-conjugated AMAB δ1.3 and phycoerythrin-conjugated anti-mouse IgM antibody (R33-24), washed and analyzed in a FACScan flow cytometer gating on lymphocytes and excluding dead cells by propidium iodide staining.

Figure 3:
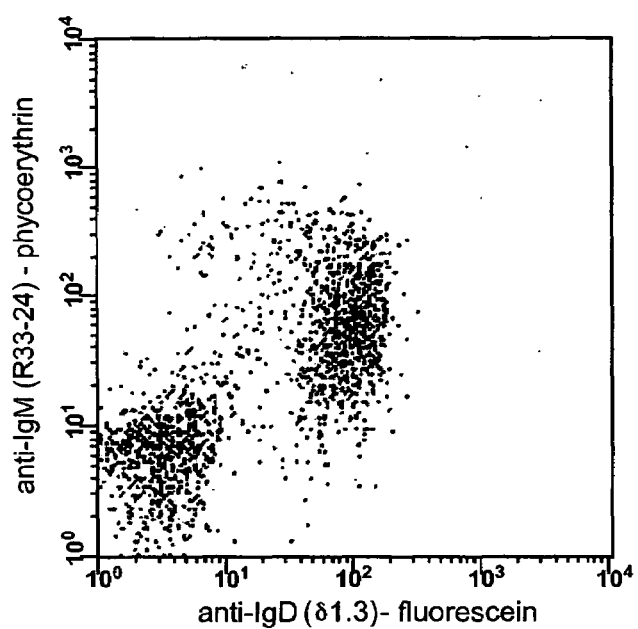
FIG. 3 depicts the results of a FACS analysis of doubly stained mouse spleen cells with anti-IgM and anti-IgD antibodies.

The results obtained are depicted in FIG. 3. The results indicate that most IgM bearing cells coexpress IgD; however, a few IgM$^+$ IgD$^-$ cells were obtained. This staining is in good accordance with the expected staining pattern for IgD. It also shows that the AMABs bind to molecules usually present in normal mice, and therefore are autologous monoclonal antibodies.

EXAMPLE 8

Magnetic Separation of Cells Using Autologous Monoclonal Antibodies Coupled to Colloidal Magnetic Particles Conjugation of antibodies to magnetic particles:

Purified AMABs δ1.3 and δ3.5 were conjugated to MACS amino microbeads (Miltenyi Biotec GmbH, Bergisch Gladbach, Germany) using SPDP (Pierce) coupling chemistry according to the instructions of the supplier. Approximately 200 μg of activated antibody were conjugated to 1 ml of SPDP modified MACS amino microbeads (OD450=10). The conjugated beads were purified twice using a MACS A1 column and rebuffered in PBS to a concentration of OD450=1 (see; Miltenyi et al. (1990).

Magnetic labelling of cells:

10 million spleen cells in 80 μl were incubated for 15 minutes at 4° C. with a 1 to 5 dilution of δ1.3 and δ3.5 conjugated magnetic particles, then the same fluorescein conjugated AMAB was added to a final concentration of 8 μg/ml. Cells were allowed to react with the antibody for 5 minutes then washed once using PBS. Magnetically and fluorescently labelled cells were separated using a MACS magnetic cell sorter (Miltenyi Biotec GmbH) according to the instructions of the supplier. The cells were applied to a prefilled A2 MACS column running with a 25G flow restrictor, the column was washed with 4 ml of buffer and cells passing through the column were collected as the unmagnetic fraction. The column was washed using one backflush procedure using a 23G flow resistor and the retained cells were eluted. All fractions were analyzed by flow cytometry (FACScan). Dead cells were identified by propidium iodide staining and were excluded from analysis.

Figure 4:
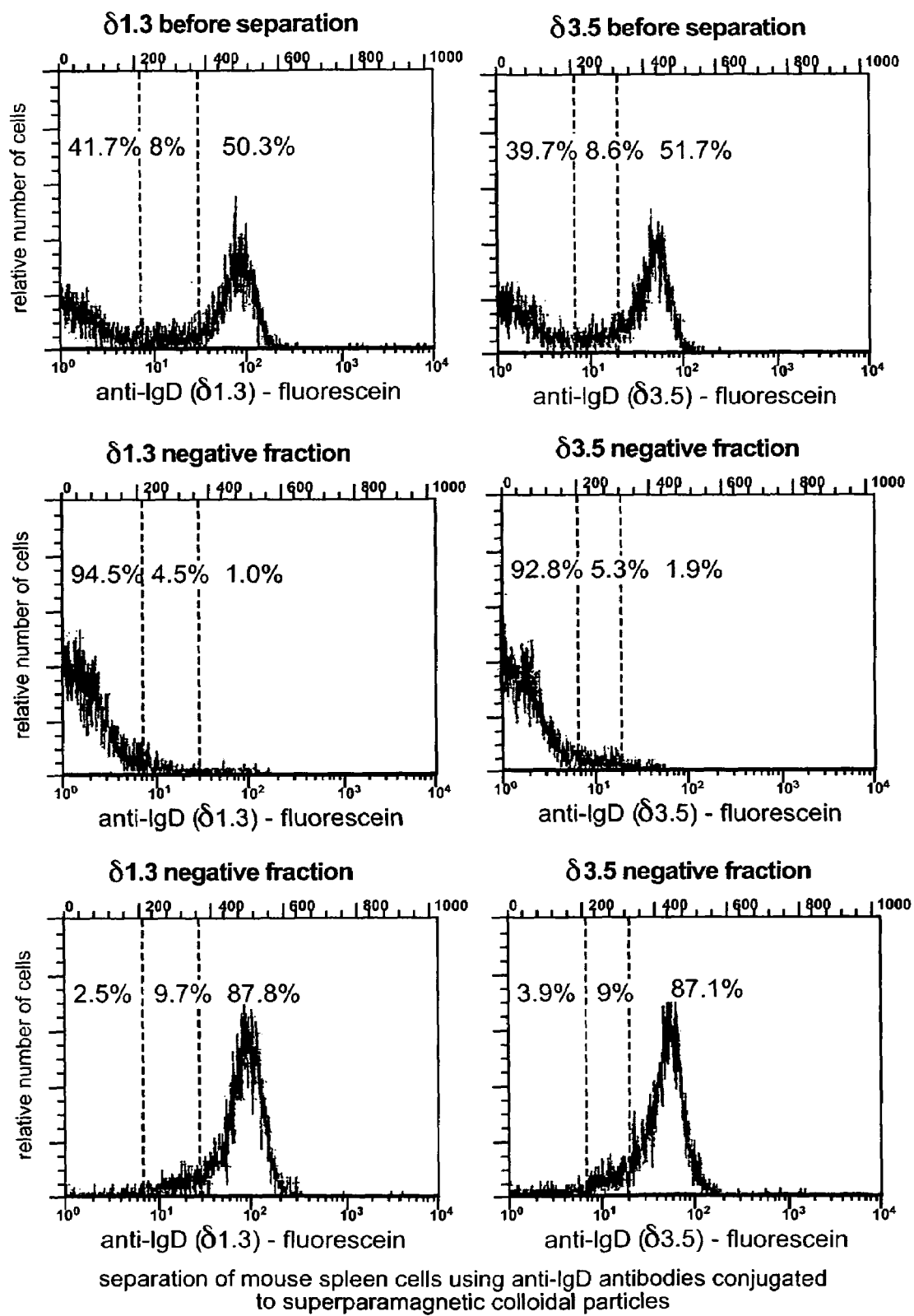
FIG. 4 depicts the results of separation of mouse spleen cells using anti-IgD antibodies conjugated to colloidal superparamagnetic particles.

FIG. 4 shows the histograms of a FACS analysis of the separations. In FIG. 4, the first row depicts the cells before separation, the second row depicts the unmagnetic fraction, and the third row depicts positive cells. δ1.3 results are in the left column, and δ3.5 results are in the right column. The data indicate that at least 95% of the IgD expressing cells are retained by the column, whereas the IgD cells being retained and eluted from the column have a purity of at least 92%. Background staining in this separation and analysis is mainly caused by macrophages taking up antibodies in an unspecific manner.

EXAMPLE 9

Obtaining NCAM Knockout Mice

Neural cell adhesion molecules (NCAMs) are members of the immunoglobulin super family mediating homo- and heterophilic cell—cell interactions. NCAMs appear in various isoforms generated by alternative splicing. Hemperly et al. (1986) Proc. Natl. Acad. Sci. USA 83:3037–3041; Barthels et al. (1987) EMBO J. 6:907–914; and Barthels et al. (1992) Eur. J. Neurosci. 4:327–337. During embryonic development, NCAMs are expressed in derivatives of all three germ layers whereas in the adult animal they are predominantly present in neural tissue. Processes like neurulation, axonal outgrowth, histogenesis of the retina and development of the olfactory system are correlated with the regulated expression of NCAMs. Crossin et al. (1990) Exp. Neurol. 109:6–18, Tosney et al. (1986) Dev. Biol. 114: 437–452; Thiery et al. (1977) J. Biol. Chem. 252:6841–6845; Key et al. (1990) J. Cell Biol. 110:1729–1743; and Chung et al. (1991) J. Comp. Neurol. 314:290–305. Homozygous NCAM-negative mice generated by gene targeting appear healthy and fertile. Adult mutants show a 10% reduction of overall brain weight and a 36% decline in size of the olfactory bulb. NCAM-deficiency coincides with the almost total loss of protein-bound α-(2,8)-linked polysialic acid, a carbohydrate structure thought to be correlated with neural development and plasticity. Theodosis et al. (1991) Proc. Natl. Acad. Sci. USA 88:5494–5498. Testing the animals in the Morris water maze as described by Morris (1981) Learn. Motiv. 12:239–260, showed deficits in spatial learning, whereas activity and motoric abilities of mutant mice appeared normal.

Gene targeting and generation of homozygous mutant mice were performed using standard protocols and confirmed by Southern blotting and allele-specific PCR. Nuclease SI protection assays, Northern and Western Blotting confirmed the targeted locus as a null-allele. Immunocytochemical analysis of brain sections for NCAM using monoclonal antibodies and polyclonal sera showed most intense staining in the glomeruli and granular cell layer of the olfactory bulb in wild type and heterozygous animals. Overall staining was in good agreement with reports on NCAM-expression in the adult brain. Chung et al. (1991). In homozygous mutant mice there was a total loss of NCAM immunoreactivity as expected.

Heterozygous animals of two lines were mated and gave rise to 78 offspring. Of these, 38 animals (49%) were heterozygous, 22 (28%) were wild type and 18 (23%) were homozygous for the mutated allele, indicating an almost perfect Mendelian distribution. Homozygous mutant animals are fertile and appear healthy up to four months of age even though they are about 10% smaller by weight than wild type and heterozygous littermates. Isolated brains of a mutant and a heterozygous animal had obvious anatomical differences: the olfactory bulb was reduced in size in mutants compared to +/+ and +/− animals; and the brain weight was reduced by about 10% (after correction for body weight).

In order to generate high affinity AMABs to NCAMs, the mice described above are inoculated with an antigenic amount of an NCAM suspended in a suitable adjuvant. Booster shots are given as required and the antibody titer is measured periodically. Once the titer is sufficient, a suitable method for generation of AMABs is followed.

All publications and patent applications cited in this specification are incorporated herein by reference to the same extent as if each individual publication or patent application was specifically and individually indicated to be incorporated by reference.

Although the foregoing invention has been described in some detail by way of illustration and example for purposes of clarity and understanding it will be apparent to those skilled in the art that certain modifications may be practiced. Therefore, the description and examples should not be construed as limiting the scope of the invention, which is delineated by the appended claims.

We claim:

1. A method for producing an antibody, or antibody fragment, that binds an epitope of a mouse self-antigen, comprising the steps of:
   (a) producing a mouse having a genome altered to knock out the expression of at least one epitope of the self-antigen of the mouse, wherein said mouse is homozygous for a mutation in the gene encoding the self-antigen;
   (b) immunizing said mouse, or progeny thereof, with an antigen to elicit an antibody response to the self-antigen epitope, wherein said antigen is said self-antigen or fragment thereof or human homolog of said self-antigen or a fragment thereof;
   (c) collecting mouse cells that produce antibodies that bind the self-antigen epitope; and
   (d) immortalizing an antibody-producing cell from step (c) to produce a hybridoma capable of continuously secreting an antibody that binds the self-antigen epitope.

2. A method for producing an antibody, or antibody fragment, that binds an epitope of a mouse self-antigen comprising the steps of:
   (a) obtaining a mouse with a genome altered by mutation of the gene or genes encoding the self-antigen to knock out the expression of at least one epitope of the self-antigen of the mouse;
   (b) immunizing said mouse with an antigen to elicit an antibody response to the self-antigen epitope, wherein said antigen is the self-antigen or fragment thereof or human homolog of said self-antigen or a fragment thereof;
   (c) collecting mouse cells that produce antibodies that bind the self-antigen epitope; and
   (d) immortalizing an antibody-producing cell from step (c) to produce a hybridoma capable of continuously secreting an antibody that binds the self-antigen epitope.

3. The method of claim 2 wherein the antibody, or antibody fragment, also binds a human protein homolog of the mouse self-antigen.

4. A method for producing an antibody, or antibody fragment, that binds an epitope of a human homolog of a mouse self-antigen comprising the steps of:
   (a) obtaining a mouse with a genome altered by mutation of the gene or genes encoding the self-antigen to knock out the expression of at least one epitope of the mouse self-antigen;
   (b) immunizing said mouse with the human homolog of the mouse self-antigen or a fragment thereof, to elicit an antibody response to the human homolog;
   (c) collecting mouse cells that produce antibodies that bind the self-antigen epitope; and
   (d) immortalizing an antibody-producing cell from step (c) to produce a hybridoma capable of continuously secreting an antibody that binds the self-antigen epitope.

5. The method of claim 1, further comprising producing an antibody or antibody fragment that binds the self-antigen epitope using genetic material derived from a mouse cell collected in step (c).

6. The method of claim 2, further comprising producing an antibody or antibody fragment that binds the self-antigen epitope using genetic material derived from a mouse cell collected in step (c).

7. The method of claim 3, further comprising producing an antibody or antibody fragment that binds the self-antigen epitope using genetic material derived from a mouse cell collected in step (c).

8. The method of claim 4, further comprising producing an antibody or antibody fragment that binds the self-antigen epitope using genetic material derived from a mouse cell collected in step (c).

* * * * *